(12) United States Patent
Fitzpatrick

(10) Patent No.: US 6,387,963 B1
(45) Date of Patent: May 14, 2002

(54) METHANOL SYNTHESIS

(75) Inventor: Terence James Fitzpatrick, Middlesbrough (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/714,486

(22) Filed: Nov. 17, 2000

Related U.S. Application Data

(63) Continuation of application No. PCT/GB99/01335, filed on Apr. 29, 1999.

(30) Foreign Application Priority Data

| May 20, 1998 | (GB) | 9810700 |
| May 28, 1998 | (GB) | 9811355 |
| Mar. 2, 1999 | (GB) | 9904649 |

(51) Int. Cl.$^7$ .............................................. C07C 27/00
(52) U.S. Cl. ...................... 518/706; 518/700; 518/702; 518/704; 518/706; 518/711
(58) Field of Search ................................ 518/702, 700, 518/706, 704, 711

(56) References Cited

U.S. PATENT DOCUMENTS 5,512,599 A * 4/1996 Hiramatsu et al. .......... 518/703
5,631,302 A * 5/1997 Konig et al. ................. 518/706

FOREIGN PATENT DOCUMENTS

EP 0 790 226 8/1997

* cited by examiner

*Primary Examiner*—Sreeni Padmanabhan
*Assistant Examiner*—J. Parsa
(74) *Attorney, Agent, or Firm*—Pillsbury Winthrop LLP

(57) ABSTRACT

Methanol is synthesised in a synthesis loop wherein recycled unreacted gas, optionally together with part of the make-up gas, is passed through a bed of synthesis catalyst under methanol synthesis conditions, make-up gas is then added and the mixture passed through at least one further bed of synthesis catalyst under methanol synthesis conditions prior to separation of the synthesised methanol. Preferably the further bed of synthesis catalyst is located in a heat exchange reactor producing pressurised hot water which is employed to saturate a hydrocarbon feedstock from which the make-up gas is produced by steam reforming.

8 Claims, 2 Drawing Sheets

METHANOL SYNTHESIS

This is a Continuation of: International Application No. PCT/GB99/01335 filed Apr. 29, 1999.

BACKGROUND OF THE INVENTION

This invention relates to methanol synthesis. Methanol is conventionally synthesized at elevated and pressure in a methanol synthesis loop where synthesis gas, containing hydrogen, carbon oxides, and, usually, some inerts such as nitrogen and methane, is passed over a copper catalyst at an elevated temperature, typically 200–300° C., and pressure, typically 40–150 bar abs., and then the product reacted gas is cooled, condensed methanol is separated and the unreacted gas is recycled to the synthesis reactor. Fresh synthesis gas, hereinafter termed make-up gas, is added to the loop at a suitable location, usually to the recycled unreacted gas before the latter is fed to the synthesis reactor. A purge is taken from the loop at a suitable point to avoid the build-up of inerts to an uneconomically high level. The make-up gas may be added to the loop before or after the separation step.

Methanol synthesis is an exothermic process and it is necessary to limit the amount of reaction occurring in a bed of catalyst and/or to cool the bed, to avoid overheating the catalyst. To this end, a variety of reactor types have been employed. For example, it has been proposed to employ a reactor with means to inject cool quench gas (generally a mixture of make-up gas and unreacted recycle gas) into the catalyst bed or between beds. Examples of such quench bed reactors are described in GB 1105614, EP 0297474, EP 0359952 and U.S. Pat. No. 4,859,425. It has also been proposed to employ reactors having heat exchangers within the beds so that heat evolved by the reaction is transferred to a coolant. Thus, in the arrangement described in U.S. Pat. No. 4,778,662 the synthesis reactor has coolant tubes which extend through at least the inlet part of the catalyst bed and open into the space above the inlet to the catalyst bed: the coolant is the mixture of recycled unreacted gas and make-up gas so that the reactants are heated to the desired inlet temperature by the evolved heat. In the arrangement described in GB 2046618 the catalyst is disposed as a single bed through which the reactants flow radially and heat exchange tubes are provided through which a coolant, e.g. pressurized boiling water, is circulated.

It is often desirable to increase the amount of methanol synthesized. In U.S. Pat. No. 5,252,609 and U.S. Pat. No. 5,631,302 methods are described wherein the make-up gas is subjected to a preliminary synthesis step before it is added to the synthesis loop. In EP 0790226 an arrangement is described where there are two synthesis reactors in series in the loop; the first reactor being cooled by heat exchange with boiling water while the second is cooled by heat exchange with the mixture of make-up gas and recycled unreacted gas.

The throughput may also be increased by operating the loop at a lower circulation ratio, which is defined herein as the ratio of the flow rate of the gas recycled from the separator to the rate at which make-up gas is fed to the loop. In a conventional methanol synthesis process, this circulation ratio is generally in the range 3 to 7. In the present invention, low circulation ratios may be employed, generally in the range 1 to 4, particularly 1 to 3, and preferably below 2.5, especially below 2. However the use of a preliminary synthesis step, or operation at low circulation ratios, has the problem that the partial pressures of the reactants of the gas fed to the preliminary synthesis step, or to the first synthesis stage of the loop, may be relatively high leading to excessive reaction, and excessive heat evolution in the catalyst bed.

We have devised a method whereby this problem may be overcome. In the present invention, methanol synthesis is effected in one or more synthesis stages from recycled unreacted gas, to which part of the make-up gas may have been added, and then the remainder of the make-up gas is added and the mixture passed through one or more further synthesis stages with at least the final synthesis stage of the loop being effected in indirect heat exchange with pressurized water as a coolant.

SUMMARY OF THE INVENTION

According to the present invention we provide a process wherein methanol is synthesized in a synthesis loop from a synthesis gas mixture comprising hydrogen and carbon oxides in at least two synthesis stages, characterised in that methanol is synthesized from recycled unreacted gas, optionally together with part of the make-up gas, in one or more synthesis stages to give a stream of reacted gas, make-up gas is then added and, prior to separation of the synthesized methanol, a further amount of methanol is synthesized from the resultant mixture in one or more further synthesis stages, with at least the final synthesis stage of the loop being effected in indirect heat exchange with pressurized water as a coolant.

In its simplest form the synthesis loop has two stages of methanol synthesis with make-up gas being added between the stages and at least the final synthesis stage of the loop is effected in indirect heat exchange with pressurised water as a coolant. The reactor used for synthesis in indirect heat exchange with pressurised water is herein termed a water-cooled reactor.

The first stage is preferably effected in a quench reactor or a heat exchange reactor wherein the synthesis catalyst is cooled by transferring heat evolved by the synthesis reaction by heat exchange to the feed gas of that reactor, e.g. as described in the aforesaid U.S. Pat. No. 4,778,662. Where more than two stages are employed, it is again preferred that the first stage is effected in a quench reactor or a heat exchange reactor as aforesaid and at least the last of the subsequent stage or stages is effected in the water-cooled reactor.

It is preferred that at least 5% of the make-up gas is added to the recycled unreacted gas before the latter is fed to the first synthesis stage. It is preferred that at least 10%, particularly at least 30%, of the make-up gas is added to the loop after the first synthesis stage, especially if the circulation rate is low, e.g. below 2. The proportion of the make-up gas that is added to the loop after the first synthesis stage will depend upon the type of reactor employed for the first synthesis stage and on the circulation ratio.

The first synthesis stage is preferably effected adiabatically.

Thus in one form of the invention, the first stage employs a quench reactor wherein some or all of the recycled unreacted gas, optionally to which part of the make-up gas has been added, is fed to the inlet and the remainder of the recycled unreacted gas, optionally in admixture with some of the make-up gas is used as the quench gas. The remainder of the make-up gas is added to the gas from the outlet of the quench reactor and the mixture is then fed to the water-cooled reactor.

Where a quench reactor is employed for the first synthesis stage, typically only about 20–25% of the recycled unreacted gas is fed to the quench reactor inlet: the balance, to which make-up gas may be added, is used as the quench gas. The quench reactor may have several beds of synthesis catalyst with injection of quench gas between each bed. With such a reactor it is preferred that at least 50% of the make-up gas is added to the reacted gas from the quench reactor after the first synthesis stage, i.e. before it is fed to the water-cooled reactor and, optionally, as part or all of the quench gas.

Where a heat exchange reactor, e.g. of the type described in U.S. Pat. No. 4,778,662, wherein the catalyst is cooled by transferring heat evolved by the synthesis reaction by heat exchange to the feed gas to that reactor, is employed for the first stage, a larger proportion, for example 30 to 90%, particularly 40 to 70%, of the make-up gas may be added to the recycled unreacted gas before the latter is fed to the first synthesis stage. After leaving the first synthesis stage, the remainder of the make-up gas is added and the mixture passed through one or more further catalyst beds, disposed in the water-cooled reactor.

The water-cooled reactor may have the catalyst disposed in tubes with the pressurized water circulating past the exterior of the tubes. However it is preferred that the catalyst is disposed as a single bed with the pressurized water passing through cooling tubes disposed within the catalyst bed.

The make-up gas is often produced by a steam reforming process wherein a hydrocarbon feedstock, such as natural gas, is reacted with steam at an elevated pressure, e.g. in the range 20 to 80 bar abs., and at an elevated temperature, e.g. in the range 700 to 1100° C., in the presence of a catalyst. This reforming reaction is strongly endothermic and at least part of the reforming reaction is generally operated with the catalyst disposed in tubes through which the feedstock/steam mixture passes while the tubes are heated externally by a suitable medium.

In the present invention, the heated pressurized water from the water-cooled reactor may be employed to supply at least part of the steam required for making the make-up gas. Thus the heated pressurized water, preferably after further heating, is directly contacted with the hydrocarbon feedstock before the latter is subjected to the reforming reaction. Such direct contact of the hydrocarbon feedstock with hot water is herein termed saturation. It will be appreciated that since the water is contacted directly with the hydrocarbon feedstock, the pressure of the pressurized water is equal to or greater than that employed in the reforming reaction. Normally, the feedstock, e.g. natural gas, at an elevated pressure is subjected to desulphurisation prior to reforming. It is generally desirable to effect the contacting with the pressurized water after any such desulphurisation step.

In a preferred arrangement, the reforming is effected in two stages. In the first, primary reforming, stage the feedstock/steam mixture is passed over a steam reforming catalyst, usually nickel supported on an inert support, e.g. alumina or a calcium aluminate cement, disposed in externally heated tubes. In the second stage, the primary reformed gas mixture is subjected to a secondary reforming stage wherein it is partially combusted with oxygen and passed through a secondary reforming catalyst. The secondary reforming catalyst is normally disposed as a single bed, again usually of nickel supported on an inert support, e.g. alumina or a calcium aluminate cement. By adjusting the amount of oxygen employed relative to the amount of feedstock, a secondary reformed gas that approximates to the stoichiometric composition for methanol synthesis may be obtained. If the secondary reforming stage is omitted, the reformed gas is liable to have an excess of hydrogen over that required for methanol synthesis, especially where the feedstock is natural gas. In a preferred version of a reforming process employing primary and secondary reforming, the primary reforming is effected in a heat exchange reformer with the heating required for the primary reforming stage being provided by passing the secondary reformed gas past the tubes containing the primary reforming catalyst.

The reformed gas is cooled and excess steam condensed therefrom before compression, if any, of the reformed gas to the synthesis loop pressure. The cooling of the reformed gas preferably includes further heating of the pressurized water before the latter is contacted with the hydrocarbon feedstock. It may also include other heat recovery, e.g. heating of pressurized water fed to the synthesis reactor, and the provision of heat for distillation of product methanol.

BRIEF DESCRIPTION OF THE DRAWINGS

The invention is illustrated by reference to the accompanying drawings wherein.

DETAILED DESCRIPTION OF THE INVENTION

Figure 1:
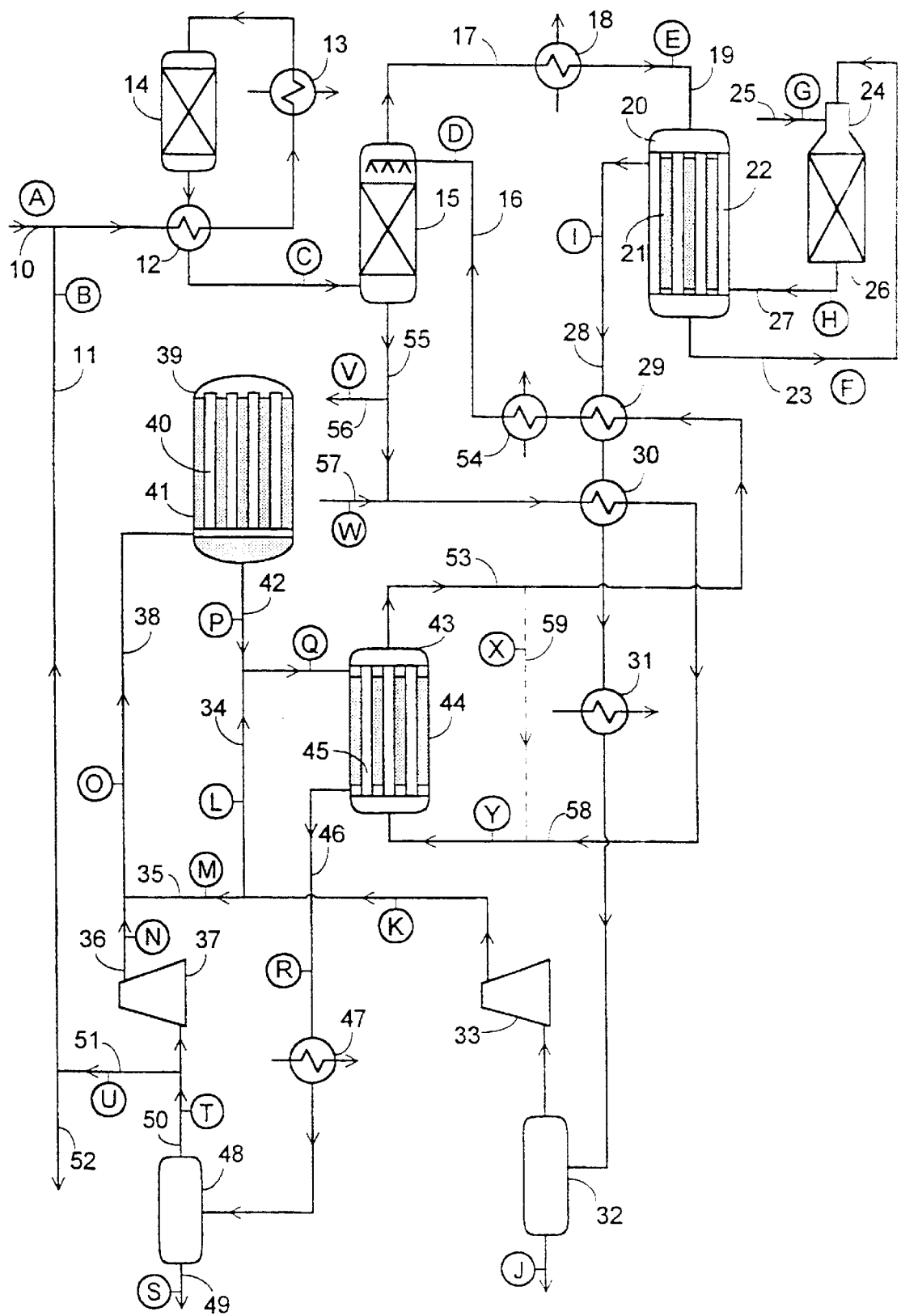
FIG. 1 is a flowsheet of one embodiment of the invention.

Referring to FIG. 1, a hydrocarbon feedstock, such as natural gas, at elevated pressure, e.g. 45 bar abs., is fed as stream A via line 10, mixed with a hydrogen-containing gas 11 (stream B), and fed to heat exchangers 12 and 13 wherein it is heated to a temperature suitable for desulphurisation. The gas is passed through a bed of a hydrodesulphurisation catalyst, e.g. nickel and/or cobalt molybdate, and a bed of a sulphur absorbent, e.g. zinc oxide, in vessel 14 to effect desulphurisation of the gas. The desulphurised gas serves as the heating medium in heat exchanger 12 and then is passed as stream C to a saturator 15. In saturator 15, the desulphurised feedstock is contacted with heated water, at a pressure similar to that of the desulphurised feedstock, fed as stream D via line 16. The saturated feedstock, i.e. a feedstock/steam mixture, is then fed via line 17 to a heater 18 where it is further heated and then fed via line 19 as stream E to a heat exchange reformer 20. Heat exchange reformer 20 has a plurality of tubes 21 containing a steam reforming catalyst, e.g. nickel supported on a calcium aluminate cement rings. The reformer tubes 21 are heated by a hot gas flowing through the shell space 22 of the heat exchange reformer 20. The feedstock/steam mixture undergoes primary reforming in the tubes 21 and is then fed as stream F via line 23 to a secondary reformer 24. in secondary reformer 24, the primary reformed gas is partially combusted with oxygen fed as stream G via line 25 and the partially combusted mixture is fed through a bed 26 of a secondary reforming catalyst, e.g. nickel supported on a support of calcium aluminate cement, where it undergoes secondary reforming. The resultant hot gas, comprising hydrogen and carbon oxides plus unreacted steam and a little unreacted methane, is then fed as stream H via line 27 to the shell space 22 of the heat exchange reformer wherein it serves to heat the reformer tubes 21. The partially cooled secondary reformed gas leaves the heat exchange reformer 20 as stream I via line 28. The secondary reformed gas is then further cooled by heat exchange in heat exchangers 29, 30 and 31 to below the dew point of the steam in the secondary reformed gas. The unreacted steam thus condenses and is separated as stream J from the secondary reformed gas in a separator 32. The resultant dewatered gas is then compressed in compressor 33 to form fresh synthesis gas, i.e. the make-up gas, (stream K)

at about the desired synthesis pressure. The make-up gas is fed to a synthesis loop via line 34 (stream L) and, optionally also via line 35 (stream M).

In the synthesis loop, any make-up gas that is fed via line 35 is mixed with recycled unreacted gas supplied as stream N via line 36 from a circulator 37. The resultant mixture, stream O, is then fed via line 38 to a heat exchange reactor 39. The synthesis gas passes up through tubes 40 surrounded by a bed 41 of methanol synthesis catalyst. The synthesis catalyst is typically the product of reducing to copper metal the copper oxide in a catalyst precursor containing oxides of copper, and other metals such as zinc, chromium, aluminium, magnesium and/or rare earths. Copper/zinc oxide/alumina catalysts are preferably employed. As the gas passes up through tubes 40 it is heated to the desired synthesis inlet temperature, which is typically in the range 200 to 240° C., and then passes down through the bed of synthesis catalyst. Methanol synthesis occurs with heat evolved heating the incoming gas passing up through tubes 40. The resultant reacted gas, comprising methanol and unreacted gas, is then passed as stream P via line 42 to a water-cooled reactor 43.

Make-up gas is supplied via line 34 as stream L and added to the mixture to give stream Q before it enters water-cooled reactor 43. In reactor 43, the partially reacted synthesis gas passes through a bed 44 of methanol synthesis catalyst through which pass a plurality of tubes 45 through which water at a pressure substantially equal to the reforming pressure, e.g. 45 bar abs., is passed as a coolant. More methanol synthesis occurs as the gas passes through the bed 44 with the heat evolved heating the pressurised water. The reacted gas leaves the water-cooled reactor 44 as stream R via line 46 and is cooled, to below the dew point of the methanol therein, in heat exchanger 47. The condensed crude methanol is separated in separator 48. and is collected as stream S via line 49. The crude methanol may then be subjected to distillation as is well known in the art.

The unreacted gas from which the crude methanol has been separated is recycled as stream T via line 50 to the circulator 37. Part of the unreacted gas is taken via line 51 as a purge stream U; part of the purge is fed as the hydrogen-containing gas fed via line 11 as stream B while the remainder is purged via line 52 and used as fuel, e.g. it may be combusted and the combustion products used to heat heat exchanger 18.

The hot pressurized water leaves water-cooled reactor 43 via line 53 and is further heated in heat exchanger 29 to provide the hot pressurized water stream D fed to the saturator 15 via line 16. In some cases it may be necessary to heat the hot pressurized water from heat exchanger 29 further in a heat exchanger 54 which may also be heated by the purge gas combustion products. The surplus water from the saturator 15 is drained via line 55. Part of the surplus water is discharged via line 56 to stream V. To the remainder make-up water is added as stream W via line 57 and the mixture heated in heat exchanger 30 and returned to the water-cooled reactor 43 via line 58.

In some cases it may be desirable to increase the temperature of the coolant water entering the water-cooled reactor 43 via line 58 by recycling part of the hot pressurized water leaving the reactor 43 via line 53 directly back to line 58 as stream X via the line 59 shown dotted in FIG. 1 so that the coolant stream Y fed to the water-cooled reactor 43 is a mixture of stream X and the water supplied via line 58. This may be desirable to prevent overcooling of the reactants in water-cooled reactor 43, i.e. preventing cooling to a temperature at which the synthesis catalyst is no longer sufficiently active.

The heat exchanger 31 may be used for preheating the make-up water feed 57 and/or to provide heat for distillation of the crude methanol. Some or all of the water separated in separator 32 as stream J and/or a methanol/water stream separated in the distillation stage, may be recycled as part of the make-up water 57.

Figure 2:
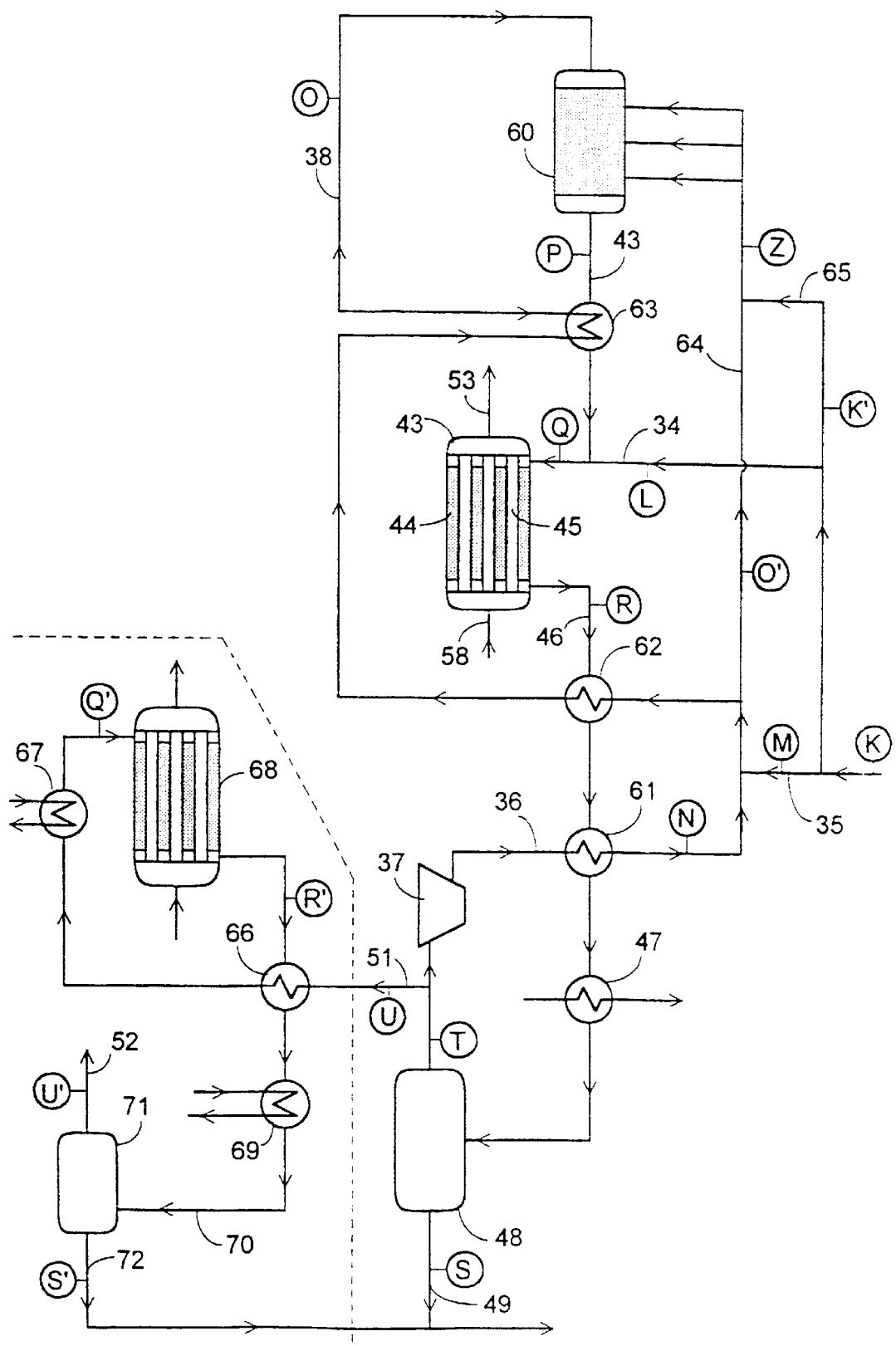
FIG. 2 is a flowsheet of an alternative methanol loop arrangement for use in the flowsheet of FIG. 1.

In the alternative methanol synthesis loop shown in FIG. 2, the heat exchange reactor 39 of FIG. 1 is replaced by a quench reactor 60 and further heat exchangers 61, 62 and 63 are provided to heat the feed to the quench reactor to the desired synthesis inlet temperature. Make-up gas may be fed as stream M to the loop via line 35 where it mixes with recycled unreacted gas (stream N) which has been heated in heat exchanger 61. Part of the resultant synthesis gas is heated in heat exchangers 62 and 63 to the desired synthesis inlet temperature and is fed as stream O via line 38 to the inlet of the synthesis reactor 60. The remainder of the synthesis gas is fed as stream O' via line 64 to the synthesis reactor 60 as quench gas. Typically quench gas is injected into the synthesis reactor 60 at a plurality of locations. The reacted gas from synthesis reactor 60 is passed via line 43 to heat exchanger 63 and then is mixed with further make-up gas supplied as stream L via line 34 and fed to the water-cooled reactor 43. The reacted gas from reactor 43 is cooled in heat exchangers 62 and 61 and then further cooled in heat exchanger 47 and then fed to the separator 48. Part of the separated unreacted gas, stream T, is fed to the circulator 37 as recycle gas while the remainder is taken from the loop as a purge stream U via line 51.

Part of the make-up gas may be diverted via line 65 as stream K' and used to augment stream O' to give the quench gas stream Z.

In FIG. 2 a further modification is shown by the region enclosed by the dotted line. Thus in order to increase further the amount of methanol formed, the purge gas stream U taken from the loop via line 51 is subjected to a further step of methanol synthesis. Thus the purge gas stream U is fed to a feed/effluent heat exchanger 66 and then to a further heat exchanger 67 where it is heated to the desired synthesis inlet temperature. The heated purge gas is then fed as stream Q' to a further synthesis reactor 68 which, like reactor 43, may be a reactor cooled by pressurized water. The reacted purge gas, stream R', is then fed to feed/effluent heat exchanger 66 and to a cooler 69 wherein it is cooled to below the dew point of the methanol therein. The cooled reacted purge gas is then fed via line 70 to a separator 71 wherein the condensed methanol is separated as stream S'. The residual unreacted gas stream U' is then taken as the purge 52 while the separated methanol is taken, via line 72, and added to the condensed methanol in line 49 separated in the loop separator 48. The hydrogen-rich gas added to the feedstock via line 11 may be taken from the purge 52.

The invention is further illustrated by the following calculated examples in which all pressures, temperatures and flow rates (in kmol/h) have been rounded to the nearest integer.

EXAMPLE 1 (comparative)

In this example the flow sheet follows the scheme of FIG. 1. The feedstock (stream A) is natural gas and the make-up water (stream W) comprises fresh water together with the condensate (stream J) separated in separator 32 and a stream of water containing some methanol separated in a stage of distillation of the crude methanol. In this comparative example all of the make-up gas (stream K) is added as stream M to the recycled unreacted gas (stream N) from the circulator 37. The loop operates at a circulation rate of 2. In order to avoid overcooling of the catalyst in the water-cooled reactor 43, a substantial proportion of the hot water leaving the reactor 43 via line 53 is recycled directly as stream X. The amount of catalyst required for the water-cooled reactor 43 is about 2½ times that required in the heat exchange reactor 39.

The flow rates, temperatures and pressures of the various streams are shown in the following Table 1.

EXAMPLE 2

In this example, the feedstock and conditions are the same as in Example 1 except that the loop operates at a circulation rate of 1 and part (about 60%) of the make-up gas stream K by-passes the heat exchange reactor 39 and is fed as stream L and added to the effluent, stream P, from the heat exchange reactor 39. In the following Table 2, the flow rates, temperatures and pressures of the streams are shown. The amount of catalyst required in the heat exchange reactor 40 is about half that required for the heat exchange reactor in Example 1 and the amount of catalyst required for the water-cooled reactor 44 is about 4% more than that required for the water-cooled reactor 44 in Example 1. Since the flow rates, temperatures and pressures of the streams, including the water streams, in the production of the make-up gas are essentially the same as in Example 1, they are omitted for brevity. The slight difference in the composition of the

TABLE 1

| Stream | T (° C.) | P (bar abs) | Flow rate (kmol/h) | | | | | | | |
|---|---|---|---|---|---|---|---|---|---|---|
| | | | $CH_4$ | CO | $CO_2$ | $H_2O$ | $H_2$ | $N_2$ | $O_2$ | $CH_3OH$ |
| A | 20 | 45 | 3409* | 0 | 22 | 0 | 12 | 16 | 0 | 0 |
| B | 40 | 45 | 20 | 4 | 17 | 0 | 105 | 4 | 0 | 1 |
| C | 230 | 45 | 3429* | 4 | 39 | 0 | 116 | 20 | 0 | 1 |
| D | 257 | 45 | 0 | 0 | 2 | 57652 | 1 | 0 | 0 | 33 |
| E | 450 | 45 | 3429* | 4 | 40 | 7652 | 117 | 20 | 0 | 34 |
| F | 693 | 40 | 2936 | 251 | 718 | 6083 | 3333 | 20 | 0 | 0 |
| G | 150 | 45 | 0 | 0 | 0 | 0 | 0 | 17 | 1669 | 0 |
| H | 975 | 40 | 224 | 2557 | 1125 | 6303 | 8536 | 37 | 0 | 0 |
| I | 528 | 39 | 224 | 2557 | 1125 | 6303 | 8536 | 37 | 0 | 0 |
| J | 40 | 38 | 0 | 0 | 2 | 6274 | 1 | 0 | 0 | 0 |
| K | 146 | 84 | 224 | 2557 | 1123 | 29 | 8535 | 37 | 0 | 0 |
| L | 0 | 0 | 0 | 0 | 0 | 0 | 0 | 0 | 0 | 0 |
| M | 146 | 84 | 224 | 2557 | 1123 | 29 | 8535 | 37 | 0 | 0 |
| N | 48 | 84 | 3278 | 706 | 2799 | 12 | 17486 | 587 | 0 | 141 |
| O | 80 | 84 | 3502 | 3263 | 3922 | 41 | 26022 | 624 | 0 | 141 |
| P | 265 | 82 | 3502 | 1857 | 3230 | 733 | 21135 | 624 | 0 | 2238 |
| Q | 265 | 82 | 3502 | 1857 | 3230 | 733 | 21135 | 624 | 0 | 2238 |
| R | 245 | 81 | 3502 | 751 | 3104 | 859 | 18545 | 624 | 0 | 3470 |
| S | 40 | 78 | 28 | 3 | 138 | 846 | 12 | 2 | 0 | 3321 |
| T | 40 | 78 | 3474 | 748 | 2967 | 13 | 18532 | 623 | 0 | 149 |
| U | 40 | 78 | 196 | 42 | 167 | 1 | 1046 | 35 | 0 | 8 |
| V | 202 | 45 | 0 | 0 | 0 | 191 | 0 | 0 | 0 | 0 |
| W | 102 | 45 | 0 | 0 | 2 | 7843 | 1 | 0 | 0 | 35 |
| X | 244 | 45 | 0 | 0 | 10 | 342101 | 4 | 0 | 0 | 198 |
| Y | 240 | 45 | 0 | 0 | 11 | 399753 | 5 | 0 | 0 | 231 |

*in addition contains 398 kmol/h of higher hydrocarbons expressed as $CH_{2.98}$ The methanol in stream S, less the amount of methanol recycled from the subsequent distillation, amounts to about 2525 tonnes per day.

makeup gas stream K results from the different composition and amount of the hydrogen-containing stream B recycled from the synthesis loop.

TABLE 2

| Stream | T (° C.) | P (bar abs) | Flow rate (kmol/h) | | | | | | |
|---|---|---|---|---|---|---|---|---|---|
| | | | $CH_4$ | CO | $CO_2$ | $H_2O$ | $H_2$ | $N_2$ | $CH_3OH$ |
| A | 20 | 45 | 3409* | 0 | 22 | 0 | 12 | 16 | 0 |
| B | 40 | 45 | 9 | 7 | 23 | 0 | 108 | 2 | 1 |
| K | 146 | 84 | 220 | 2560 | 1123 | 29 | 8513 | 35 | 0 |
| L | 146 | 84 | 132 | 1536 | 674 | 17 | 5108 | 21 | 0 |
| M | 146 | 84 | 88 | 1024 | 449 | 12 | 3405 | 14 | 0 |
| N | 49 | 84 | 772 | 602 | 1948 | 4 | 8952 | 127 | 74 |
| O | 75 | 84 | 860 | 1626 | 2397 | 16 | 12357 | 141 | 74 |
| P | 256 | 82 | 860 | 937 | 2005 | 409 | 9800 | 141 | 1156 |
| Q | 223 | 82 | 993 | 2473 | 2679 | 426 | 14908 | 162 | 1156 |
| R | 249 | 81 | 993 | 769 | 2638 | 467 | 11377 | 162 | 2901 |
| S | 40 | 78 | 12 | 4 | 164 | 462 | 12 | 1 | 2807 |

TABLE 2-continued

| Stream | T (° C.) | P (bar abs) | Flow rate (kmol/h) | | | | | | |
|---|---|---|---|---|---|---|---|---|---|
| | | | $CH_4$ | CO | $CO_2$ | $H_2O$ | $H_2$ | $N_2$ | $CH_3OH$ |
| T | 40 | 78 | 950 | 765 | 2473 | 5 | 11365 | 161 | 94 |
| U | 40 | 78 | 208 | 162 | 525 | 1 | 2413 | 34 | 20 |

*in addition contains 398 kmol/h of higher hydrocarbons expressed as $CH_{2.98}$ In this example, although the methanol production is decreased compared to Example 1, the power requirement of the circulator is only about half that of Example 1, and the total amount of catalyst required is about 89% of that required for Example 1.

EXAMPLE 3

In this example, only the synthesis loop is shown and this follows the flowsheet of FIG. 2.

Make-up gas (stream K) supplied at a rate of 27987 kmol/h at about 84 bar abs. and at a temperature of 116° C. is divided into three streams. One part, stream M, representing about 21% of the total, is fed to the synthesis loop where it is mixed with recycle gas (stream N) supplied at a rate of 55000 kmol/h from circulator 37 via heat exchanger 61. The system thus operates at a circulation rate of about 1.97. 25% of the resultant mixture of streams M and N is fed to heat exchangers 62 and 63 where it is heated and fed, as stream O, to the inlet of a quench synthesis reactor 60. The remainder (stream O') of the mixture of recycle gas and make-up gas streams N and M is then mixed with the second part (stream K') of the make-up gas to form a quench stream Z. Stream K' represents about 49% of the make-up gas. Stream Z is used as the quench gas in the quench reactor 60. The quench reactor typically has 5 beds of catalyst and is operated with bed exit temperatures progressively decreasing from 280° C. (first bed) to 260° C. (final bed). The quench gas is introduced between each bed in such proportions that the temperature of the gas leaving the previous bed is decreased to a temperature in the range 215–220° C. before the mixture of reacted gas and quench gas enters the next bed. The reacted gas (stream P) leaves the final bed at a temperature of 260° C. and at a pressure of 82 bar abs. The reacted gas stream P is cooled in heat exchanger 63 and then the remainder, about 30%, of the total make-up gas is added as stream L to give a gas stream Q at 245° C. which is fed to the water-cooled reactor 43. This reactor is operated to give an exit temperature of 222° C. The volume of catalyst employed in the water-cooled reactor 43 is about 68% of that used in the quench reactor 60. The reacted gas, at a pressure of 80 bar abs., is then fed as stream R to the heat exchanger train 62, 61 and 47 wherein it is cooled to 35° C. and fed to the separator 48. The separated crude methanol is taken as stream S while the separated unreacted gas (stream T) is divided into a recycle stream and a purge stream U. The recycle stream at a pressure of 80 bar abs. is fed to the circulator 37 where it is compressed to 84 bar abs and fed to heat exchanger 61 to give stream N.

The purge stream U is heated in heat exchangers 66, 67 to 220° C. and fed as stream Q' to a synthesis reactor 68 cooled by pressurized water. The volume of catalyst in reactor 68 is about 10.5% of that used in the quench reactor 60. More methanol is synthesized in reactor 68 to give a reacted purge gas stream R' at 79 bar abs at a temperature of 221° C. The reacted purge gas stream R' is cooled by heat exchangers 66, 69 to 35° C. and fed to separator 71. The unreacted gas is taken as the purge stream U' and the separated crude methanol stream S' is added to the crude methanol stream S from loop separator 49 to give a final crude methanol product stream.

The flow rates and temperatures of the components of the streams are shown in the following Table 3.

TABLE 3

| stream | temp (° C.) | Flow rate (kmol/h) | | | | | | |
|---|---|---|---|---|---|---|---|---|
| | | $CH_4$ | CO | $CO_2$ | $H_2O$ | $H_2$ | $N_2$ | $CH_3OH$ |
| K | 116 | 952 | 4193 | 2064 | 46 | 20648 | 84 | 0 |
| M | 116 | 200 | 881 | 433 | 10 | 4336 | 18 | 0 |
| N | 114 | 5540 | 799 | 2068 | 20 | 45861 | 501 | 212 |
| O | 223 | 1435 | 420 | 625 | 7 | 12549 | 130 | 53 |
| O' | 114 | 4305 | 1260 | 1876 | 22 | 37648 | 389 | 159 |
| K' | 116 | 467 | 2055 | 1011 | 23 | 10118 | 41 | 0 |
| Z | 115 | 4772 | 3314 | 2887 | 45 | 47765 | 430 | 159 |
| P | 260 | 6207 | 1610 | 2238 | 1327 | 52241 | 560 | 3611 |
| L | 116 | 286 | 1258 | 619 | 14 | 6194 | 25 | 0 |
| Q | 245 | 6492 | 2868 | 2857 | 1341 | 58436 | 585 | 3611 |
| R | 222 | 6492 | 934 | 2493 | 1704 | 53478 | 585 | 5908 |
| S | 35 | 35 | 2 | 83 | 1681 | 21 | 1 | 5661 |
| T | 35 | 6458 | 931 | 2410 | 23 | 53457 | 584 | 247 |
| U | 35 | 918 | 132 | 342 | 3 | 7596 | 83 | 35 |
| R' | 225 | 918 | 31 | 115 | 231 | 6710 | 83 | 364 |
| U' | 35 | 916 | 31 | 113 | 4 | 6709 | 83 | 25 |
| S' | 35 | 2 | 0 | 2 | 226 | 1 | 0 | 340 |
| S + S' | 35 | 37 | 2 | 85 | 1907 | 22 | 1 | 6001 |

EXAMPLE 4 (comparative)

By way of comparison, Example 3 was repeated but heat exchanger 63 and water-cooled reactor 44 are omitted and the reacted gas stream P from quench reactor 60 is fed directly to the exchanger train 62, 61, 47. The total amount of make-up gas (stream K) is decreased to 16804 kmol/h. The system thus operates at a circulation ratio of 3.27. Stream M forms 25% of the total make-up gas. As in Example 3, 25% of the mixture of streams M and N is fed to heat exchanger 62 and is fed as stream O to the inlet of the quench reactor 60. The remaining 75% of the mixture of streams M and N forms stream O' and is mixed with the remaining 75% of the make-up gas (stream K') to form the quench gas stream Z.

The flow rates and temperatures of the components of the streams are shown in the following Table 4.

TABLE 4

| stream | temp (° C.) | Flow rate (kmol/h) | | | | | | |
|---|---|---|---|---|---|---|---|---|
| | | $CH_4$ | CO | $CO_2$ | $H_2O$ | $H_2$ | $N_2$ | $CH_3OH$ |
| K | 116 | 572 | 2517 | 1239 | 28 | 12397 | 50 | 0 |
| M | 116 | 143 | 629 | 310 | 7 | 3099 | 13 | 0 |
| N | 99 | 5531 | 1461 | 1665 | 21 | 45612 | 500 | 210 |
| O | 218 | 1419 | 523 | 494 | 7 | 12178 | 128 | 53 |

TABLE 4-continued

| stream | temp (° C.) | Flow rate (kmol/h) | | | | | | |
|---|---|---|---|---|---|---|---|---|
| | | CH$_4$ | CO | CO$_2$ | H$_2$O | H$_2$ | N$_2$ | CH$_3$OH |
| O' | 100 | 4256 | 1568 | 1481 | 21 | 36534 | 384 | 158 |
| K' | 116 | 429 | 1888 | 929 | 21 | 9298 | 38 | 0 |
| Z | 104 | 4684 | 3456 | 2411 | 42 | 45831 | 422 | 158 |
| P | 260 | 6103 | 1609 | 1871 | 1082 | 50171 | 550 | 3613 |
| S | 35 | 21 | 2 | 40 | 1059 | 12 | 1 | 3382 |
| T | 35 | 6082 | 1607 | 1831 | 23 | 50159 | 550 | 231 |
| U | 35 | 551 | 146 | 166 | 2 | 4546 | 50 | 21 |
| R' | 221 | 551 | 12 | 50 | 118 | 3933 | 50 | 270 |
| U' | 35 | 550 | 12 | 49 | 2 | 3932 | 50 | 16 |
| S' | 35 | 2 | 0 | 1 | 116 | 1 | 0 | 254 |
| S + S' | 35 | 22 | 2 | 41 | 1174 | 13 | 1 | 3636 |

By comparison with Example 3 it is seen that the addition of the water-cooled reactor 43 and addition of part of the make-up gas between the quench reactor 60 enables a conventional synthesis loop to be uprated to increase the amount of methanol produced by about 65% without increasing the duty of the circulator 37.

What is claimed is:

1. In a process wherein methanol is synthesized in a synthesis loop from a synthesis gas comprising hydrogen and carbon oxides in at least two synthesis stages, the improvement comprising synthesizing methanol from recycled unreacted gas in at least one synthesis stage to give a stream of reacted gas, make-up gas is then added and, prior to separation of the synthesized methanol, a further amount of methanol is synthesized from the resultant mixture in at least one further synthesis stage, with at least the final synthesis stage of the loop being effected in indirect heat exchange with pressurized water as a coolant.

2. A process according to claim 1 wherein the make-up gas is produced by steam reforming of a hydrocarbon feedstock and at least part of the process steam required for the steam reforming is introduced by contacting the hydrocarbon feedstock with a stream of hot water produced in said heat exchange reactor.

3. A process according to claim 1 wherein the circulation ratio is in the range 1 to 3.

4. A process according to claim 1 wherein at least 10% of the make-up gas is added to the loop after the first synthesis stage.

5. A process according to claim 1 wherein part of the make-up gas is added to the recycled unreacted gas before the first synthesis stage.

6. A process according to claim 1 wherein the first synthesis stage is effected in a quench reactor and 50 to 95% of the make-up gas is added to the reacted gas from the quench reactor after the first synthesis stage.

7. A process according to claims 1 wherein the first synthesis stage is effected in heat exchange with the feed gas to that stage whereby heat evolved by the methanol synthesis is transferred to the feed gas and 30–90% of the make-up gas is added to the recycled unreacted gas before the latter is fed to the first synthesis stage.

8. A process according to claim 1 wherein part of the make-up gas is added to the recycled unreacted gas before the first synthesis stage and the remainder of the make-up gas is added to said reacted gas before said at least one further synthesis stage.

* * * * *